(12) United States Patent
Halamish

(10) Patent No.: US 6,883,517 B2
(45) Date of Patent: Apr. 26, 2005

(54) DOWNDRAFT NEBULIZER

(76) Inventor: Asaf Halamish, 10 Shaananim St., Perdes, Chana Karkur (IL)

(*) Notice: Subject to any disclaimer, the term of this patent is extended or adjusted under 35 U.S.C. 154(b) by 108 days.

(21) Appl. No.: 10/259,644

(22) Filed: Sep. 30, 2002

(65) Prior Publication Data

US 2004/0060556 A1 Apr. 1, 2004

(51) Int. Cl.⁷ ................................................. B05B 1/26
(52) U.S. Cl. ............................. 128/200.18; 128/200.11; 128/200.14; 128/200.21; 128/203.12; 128/203.19; 128/204.25
(58) Field of Search ....................... 128/200.11, 200.14, 128/200.18, 200.21, 203.12, 203.15, 203.16, 203.19, 204.15, 204.25; 239/338, 370, 434; 261/78.1

(56) References Cited

U.S. PATENT DOCUMENTS

| | | | |
|---|---|---|---|
| 3,232,292 A | | 2/1966 | Schaefer |
| 3,902,488 A | | 9/1975 | Sheppard |
| 3,903,884 A | * | 9/1975 | Huston et al. ......... 128/200.18 |
| 4,343,282 A | * | 8/1982 | Glenn ........................ 123/523 |
| 4,512,341 A | | 4/1985 | Lester |
| 4,554,916 A | * | 11/1985 | Watt ....................... 128/203.12 |
| 4,805,609 A | * | 2/1989 | Roberts et al. ......... 128/200.21 |
| 5,320,094 A | | 6/1994 | Laube et al. |
| 5,490,630 A | | 2/1996 | Hecker |
| 5,503,144 A | * | 4/1996 | Bacon ................... 128/203.15 |
| 5,533,501 A | | 7/1996 | Denyer |
| 5,630,409 A | * | 5/1997 | Bono et al. ............ 128/200.18 |
| 5,755,218 A | * | 5/1998 | Johansson et al. ..... 128/200.14 |
| 5,875,774 A | | 3/1999 | Clementi et al. |
| 6,014,970 A | * | 1/2000 | Ivri et al. .............. 128/200.16 |
| 6,338,443 B1 | | 1/2002 | Piper |
| 6,425,392 B1 | * | 7/2002 | Sosiak ................... 128/200.23 |
| 6,598,602 B1 | * | 7/2003 | Sjoholm ................ 128/200.16 |
| 6,681,767 B1 | * | 1/2004 | Patton et al. .......... 128/203.15 |
| 6,701,917 B1 | * | 3/2004 | O'Leary ................ 128/200.23 |
| 2004/0031484 A1 | * | 2/2004 | Halamish ............... 128/200.14 |

FOREIGN PATENT DOCUMENTS

WO  WO 02/02052  1/2002

* cited by examiner

Primary Examiner—Henry Bennett
Assistant Examiner—Amanda Wieker
(74) Attorney, Agent, or Firm—Welsh & Flaxman LLC

(57) ABSTRACT

A pneumatic nebulizer for the delivery of medications that produces aerosol mist in a downward direction. A gas inlet introduces a high velocity gas that passes through a venturi orifice producing a venture effect. A liquid stored in a reservoir is drawn into the orifice, atomizing forming droplets. The droplets are further atomized by hitting a baffle. The mist formed substantially circumscribes the baffle.

**23 Claims, 13

DOWNDRAFT NEBULIZER

FIELD AND BACKGROUND OF THE INVENTION

The present invention relates to pneumatic nebulizers and, in particular, it concerns a pneumatic nebulizer in which aerosol mist is produced in a downwardly flowing direction, the aerosol mist then leaves the nebulizer through a downwardly projecting aerosol outlet.

It is known to provide a nebulizer for the production of a high volume of aerosol for inhalent delivery of medications. In general pneumatic nebulizers atomize liquids by introducing small amounts of the liquid into a flow of high velocity air, which serves to break up the liquid into small droplets. Usually, the liquid is as drawn from a reservoir and aspirated into the airflow by means of a venturi effect created by structural elements of the device. The air and liquid mixture then continues in an upward direction to an aerosol outlet. The medicated aerosol mist is then administered to a patient by means of a therapeutic inhalation interface or by discharge of the mist into the ambient air for direct inhalation by the patient. This upward flow has become the generally accepted means for keeping drops that are too large from continuing with the upward airflow. The larger drops are then drawn by gravity back into the reservoir. This style of nebulizer in herein referred to as an "up draft" nebulizer.

Some pneumatic nebulizers, such as the up draft nebulizer of U.S. Pat. No. 6,338,443, add an additional step of impacting the high velocity air and liquid mixture onto a solid surface so as to further break up the liquid into smaller droplets, which are then drawn out through the aerosol outlet. Here too, drop which are too large fall back into the reservoir region from the force of gravity.

The nebulizer disclosed in U.S. Pat. No. 5,490,630 has a side directed aerosol outlet, herein referred to as a "side draft" nebulizer, and includes an atomization stage in which a liquid is aspirated into a downward flowing jet of air. The air/liquid mixture in then impinged upon a solid structural surface to further atomize the droplets as the flow path continues in a downward direction. The flow path is then directed upwardly toward the side directed aerosol outlet. The change of direction is used in this device as a means of separating out the larger drops from the aerosol mist.

It is obvious by their designs that the above mentioned devices are intended for deployment at a designated orientation, and that proper function is limited to a relatively small range of variance from the designated orientation. In practical use, however, it would sometimes advantageous to deploy a nebulizer at an orientation outside the tolerances of these devices. U.S. Pat. No. 4,512,341 to Lester suggests a solution by disclosing a nebulizer that is operational at any orientation between vertical and horizontal. The vertical orientation, however, is referring to an up draft configuration, therefore '341 discloses a nebulizer that is usable as both an up draft and side draft nebulizer, and any orientation in between.

Further, WO0202052, to the present inventor, discloses an aerosol inhalation interface that is suspended above the patient. It should be obvious to one ordinarily skilled in the art that while the inhalation interface of WO0202052 will function with excellent results using either up draft or side draft nebulizers, it would be preferable to use such an interface in concert with a "downdraft" nebulizer. There are also numerous applications in which downwardly directed flow of medicated aerosol is preferable.

There are also known devices generally referred to as inhalers that are used by some patients, such as asthmatics, suffering respiratory distress. These devices typically consist of a pressurized vial from which a jet of medicated droplets is discharged in a downward direction into a side opening mouthpiece. These devices, however, are intended for delivery of medicated spray over a short time span, generally less than one second in duration. That is to say, a short burst of spray. Devices of this type are not structurally nor mechanically suited, nor are they intended for delivery for an extended time period of several minutes, nor do they teach nor suggest such application.

There is therefore a need for a nebulizer having a downwardly facing aerosol outlet that is structurally configured so as to produce aerosol mist in a downward direction and that delivers a downwardly directed flow of medicated aerosol mist for a period of time. That is to say, a downdraft nebulizer.

SUMMARY OF THE INVENTION

The present invention concerns a pneumatic nebulizer in which aerosol mist is produced in a downwardly flowing direction, the aerosol mist then leaves the nebulizer through a downwardly projecting aerosol outlet.

According to the teachings of the present invention there is provided, A pneumatic nebulizer comprising: a) at least one downwardly projecting aerosol flow outlet passageway; b) at least one inlet for introduction of a flow of high velocity gas; c) at least one orifice through which the flow of high velocity gas passes thereby causing a venturi effect; d) at least one source of liquid in fluid communication with the at least one orifice such that liquid is drawn to the orifice by the venturi effect, the liquid thereby forming into drops and flowing with the high velocity gas; and e) at least one baffle upon which the flow of high velocity gas and drops are impinged so as to atomize the drops into yet smaller droplets thereby forming a mist, the baffle deployed such that a flow-path of the mist substantially circumscribes the baffle so as to reach the at least one downwardly projecting aerosol flow outlet passageway.

According to a further teaching of the present invention, the high velocity gas is compressed air.

According to a further teaching of the present invention, the source of liquid is a reservoir configured as a bottom portion of a volume within a housing of the nebulizer.

According to a further teaching of the present invention, at least a top portion of the downwardly projecting aerosol outlet passageway extends upwardly into the volume.

According to a further teaching of the present invention, the volume substantially circumscribes at least a portion of the downwardly projecting aerosol outlet passageway.

According to a further teaching of the present invention, there is also provided at least one fluid passageway configured at a radial extremity of the volume through which the fluid communication is established.

According to a further teaching of the present invention, there is also provided a fluid passageway insert deployed within the volume, the fluid passageway insert configured so as to substantially abut at least one housing surface defining the volume, the at least one fluid passageway configured as at least one surface groove configured in the surface of one of the fluid passageway insert and the housing surface.

According to a further teaching of the present invention, the volume is configured as a substantially vertical cylindrical volume such that the orifice is configured at a top of the cylindrical volume and the downwardly projecting aerosol outlet passageway is configured at a bottom of the cylindrical volume.

According to a further teaching of the present invention, the fluid passageway insert is configured substantially as a cylinder having an open end and a closed end such that the closed end is deployed adjacent to the top of the cylindrical volume, and the closed end includes at least a portion of the orifice.

According to a further teaching of the present invention, the at least one surface groove is implemented as a plurality of circumferentially spaced apart grooves in the surface of one of the fluid passageway insert and the housing surface.

According to a further teaching of the present invention, the baffle is supported substantially above the downwardly projecting aerosol outlet passageway so as to constitute a flow path obstacle around which the mist flows in order to reach the downwardly projecting aerosol outlet passageway.

According to a further teaching of the present invention, the baffle is configured substantially as a disk having a diameter larger then a diameter of a top opening of the downwardly projecting aerosol outlet passageway, the baffle being supported above the downwardly projecting aerosol outlet passageway such that a extreme radial edge of the baffle extends beyond the top opening so as to be aligned with a portion of the reservoir.

According to a further teaching of the present invention, the baffle is supported by a plurality of circumferentially spaced apart support legs.

According to a further teaching of the present invention, the baffle further includes an upwardly extending protrusion, the baffle being deployed such that the protrusion is deployed substantially under the orifice and in substantially direct alignment with a flow of the high velocity gas and the drops so as to constitute a surface upon which the impingement occurs.

According to a further teaching of the present invention, a top surface of the baffle is downwardly sloping from the protrusion to the extreme radial edge, such that excess the liquid which accumulates on the baffle flows off the baffle thereby being returned to the reservoir.

There is also provided according a further teaching of the present invention, a pneumatic nebulizer comprising: a) at least one downwardly projecting aerosol flow outlet passageway; b) at least one inlet for introduction of a flow of high velocity gas into the housing; c) at least one orifice configured in the housing through which the flow of high velocity gas passes in a thereby causing a venturi effect; d) a reservoir defined as a bottom region of volume within a housing of the nebulizer, the reservoir being in fluid communication with the at least one orifice such that liquid is drawn to the orifice by the venturi effect, the liquid thereby forming into drops and flowing with the high velocity gas, a surface defining a bottom of the volume configured so as to be substantially planar, the plane of the bottom surface being at an angle so as to form a region of confluence of the liquid in the reservoir, the fluid communication being between the region of confluence and the at least one orifice; and e) at least one baffle upon which the flow of high velocity gas and drops is impinged so as to atomize the drops into yet smaller droplets thereby forming a mist, the baffle deployed such that a flow-path of the mist substantially circumscribes the baffle so as to reach the at least one downwardly projecting aerosol flow outlet passageway.

According to a further teaching of the present invention, the high velocity gas is compressed air.

According to a further teaching of the present invention, at least a top portion of the downwardly projecting aerosol outlet passageway extends upwardly into the volume.

According to a further teaching of the present invention, the volume substantially circumscribes at least a portion of the downwardly projecting aerosol outlet passageway.

According to a further teaching of the present invention, there is also provided at least one fluid passageway configured at a radial extremity of the volume through which the fluid communication is established.

According to a further teaching of the present invention, there is also provided a fluid passageway insert deployed within the volume, the fluid passageway insert configured so as to substantially abut at least one housing surface defining the volume, the at least one fluid passageway configured as at least one surface groove configured in the surface of one of the fluid passageway insert and the housing surface.

According to a further teaching of the present invention, the volume is a substantially vertical cylindrical volume such that the orifice is configured at a top of the cylindrical volume and the downwardly projecting aerosol outlet passageway is configured at a bottom of the cylinder.

According to a further teaching of the present invention, the fluid passageway insert is configured substantially as a cylinder having an open end and a closed end such that the closed end is deployed adjacent to the top of the cylindrical volume, and the closed end includes at least a portion of the orifice, the bottom end configured with a radial bottom edge lying in a plane that is substantially parallel to the plane of the bottom surface of the volume.

According to a further teaching of the present invention, the baffle is supported substantially above the downwardly projecting aerosol outlet passageway so as to constitute a flow path obstacle around which the mist flows in order to reach the downwardly projecting aerosol outlet passageway.

According to a further teaching of the present invention, the baffle is configured substantially as a disk having a diameter larger then a diameter of a top opening of the downwardly projecting aerosol outlet passageway, the baffle being supported above the downwardly projecting aerosol outlet passageway such that a extreme radial edge of the baffle extends beyond the top opening so as to be aligned with a portion of the reservoir.

According to a further teaching of the present invention, the baffle is supported by a plurality of circumferentially spaced apart support legs.

According to a further teaching of the present invention, the baffle further includes an upwardly extending protrusion, the baffle being deployed such that the protrusion is deployed substantially under the orifice and in substantially direct alignment with a flow of the high velocity gas and the drops so as to constitute a surface upon which the impingement occurs.

According to a further teaching of the present invention, a top surface of the baffle is downwardly sloping from the protrusion to the extreme radial edge, such that excess the liquid which accumulates on the baffle flows off the baffle thereby being returned to the reservoir.

There is also provided according to a further teaching of the present invention, a method for atomizing a liquid using a pneumatic nebulizer, the method comprising: a) providing a downward flow of high velocity gas; b) passing the downward flow of high velocity gas through at least one orifice, thereby causing a venturi effect; c) providing at least one source of liquid in fluid communication with the at least one orifice such that liquid is drawn to the orifice by the venturi effect, the liquid thereby forming into drops and flowing downwardly with the high velocity gas; and d) proving at least one baffle upon which the downward flow of high velocity gas and drops are impinged so as to atomize the drops into yet smaller droplets thereby forming a mist, the baffle deployed such that a flow-path of the mist substantially circumscribes the baffle so as to reach at least one downwardly projecting aerosol flow outlet passageway.

According to a further teaching of the present invention, the high velocity gas is implemented as compressed air.

According to a further teaching of the present invention, the source of liquid is implemented as a reservoir configured as a bottom portion of a volume within a housing of the nebulizer.

According to a further teaching of the present invention, the volume is implemented so as to substantially circumscribe at least a top portion of the downwardly projecting aerosol outlet passageway.

According to a further teaching of the present invention, there is also provided at least one fluid passageway configured at a radial extremity of the volume through which the fluid communication is established.

According to a further teaching of the present invention, there is also provided a fluid passageway insert deployed within the volume, the fluid passageway insert configured so as to substantially abut at least one housing surface defining the volume, the at least one fluid passageway configured as at least one surface groove configured in the surface of one of the fluid passageway insert and the housing surface.

According to a further teaching of the present invention, the volume is implemented as a substantially vertical cylindrical volume such that the orifice is configured at a top of the cylindrical volume and the downwardly projecting aerosol outlet passageway is configured at a bottom of the cylindrical volume.

According to a further teaching of the present invention, the fluid passageway insert is implemented substantially as a cylinder having an open end and a closed end such that the closed end is deployed adjacent to the top of the cylindrical volume, and the closed end includes at least a portion of the orifice.

According to a further teaching of the present invention, the at least one surface groove is implemented as a plurality of circumferentially spaced apart grooves in the surface of one of the fluid passageway insert and the housing surface.

According to a further teaching of the present invention, the baffle is implemented so as to be supported substantially above the downwardly projecting aerosol outlet passageway so as to constitute a flow path obstacle around which the mist flows in order to reach the downwardly projecting aerosol outlet passageway.

According to a further teaching of the present invention, the baffle is implemented substantially as a disk having a diameter larger then a diameter of a top opening of the downwardly projecting aerosol outlet passageway, the baffle being supported above the downwardly projecting aerosol outlet passageway such that a extreme radial edge of the baffle extends beyond the top opening so as to be aligned with a portion of the reservoir.

According to a further teaching of the present invention, the baffle is implemented so as to be supported by a plurality of circumferentially spaced apart support legs.

According to a further teaching of the present invention, there is also provided an upwardly extending protrusion on a top surface of the baffle, the baffle being deployed such that the protrusion is deployed substantially under the orifice and in substantially direct alignment with a flow of the high velocity gas and the drops so as to constitute a surface upon which the impingement occurs.

According to a further teaching of the present invention, the baffle in implemented having a top surface that is downwardly sloping from the protrusion to the extreme radial edge, such that excess the liquid which accumulates on the baffle flows off the baffle thereby being returned to the reservoir

BRIEF DESCRIPTION OF THE DRAWINGS

The invention is herein described, by way of example only, with reference to the accompanying drawings, wherein.

DESCRIPTION OF THE PREFERRED EMBODIMENTS

Figure 1:
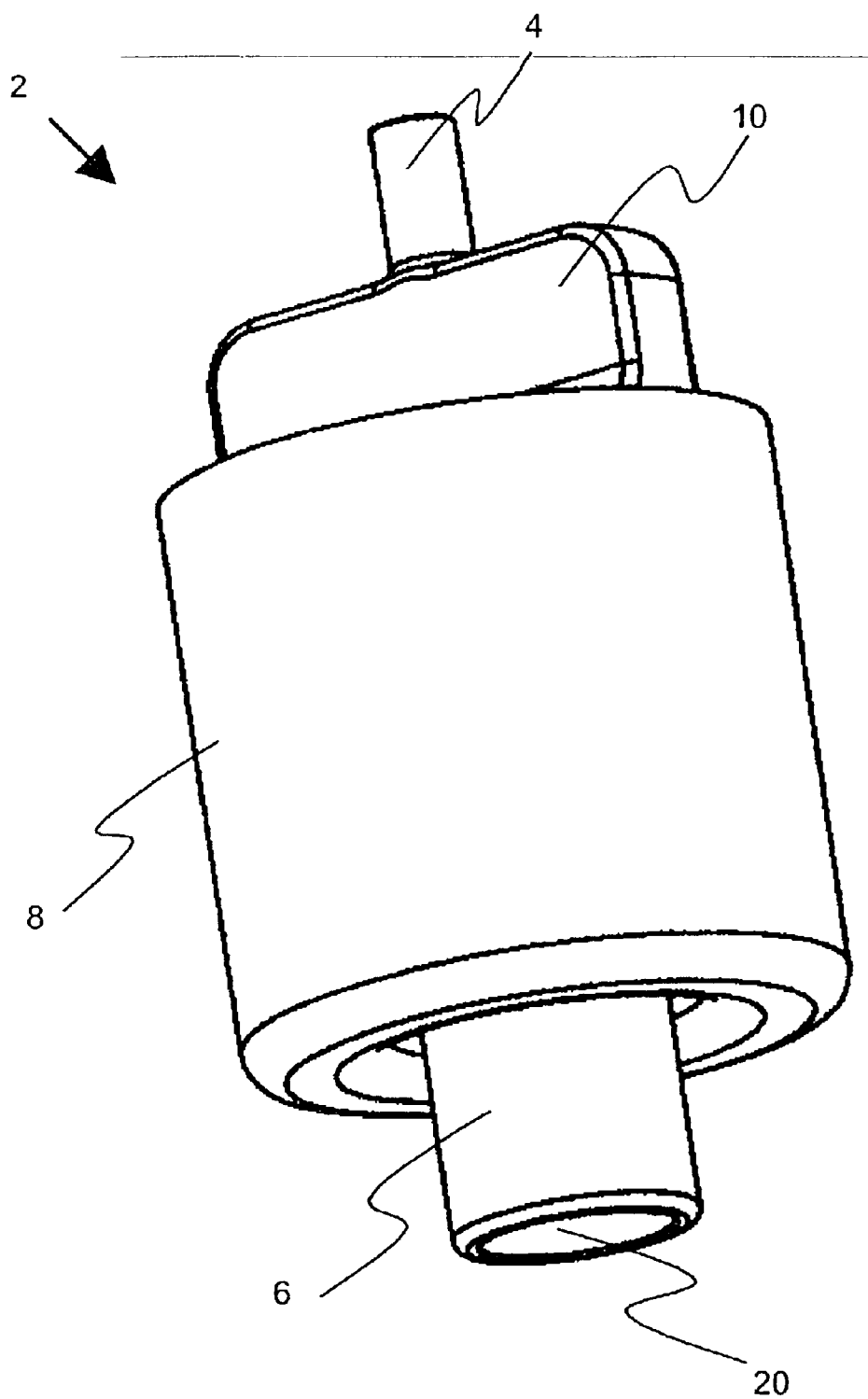
FIG. 1 is a side perspective view of a first preferred embodiment of a downdraft nebulizer constructed and operative according to the teachings of the present invention.
Figure 2:
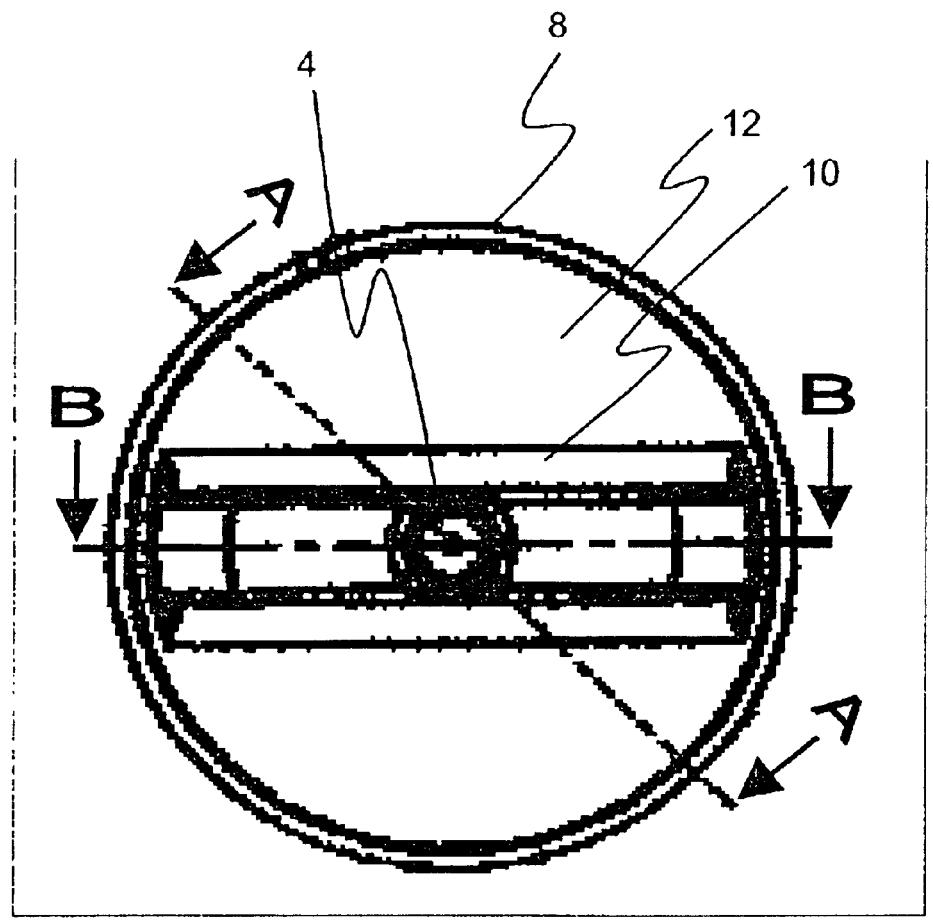
FIG. 2 is a top elevation of the embodiment of FIG. 1, which serves to establish cross-sectional lines A—A and B—B.
Figure 3:
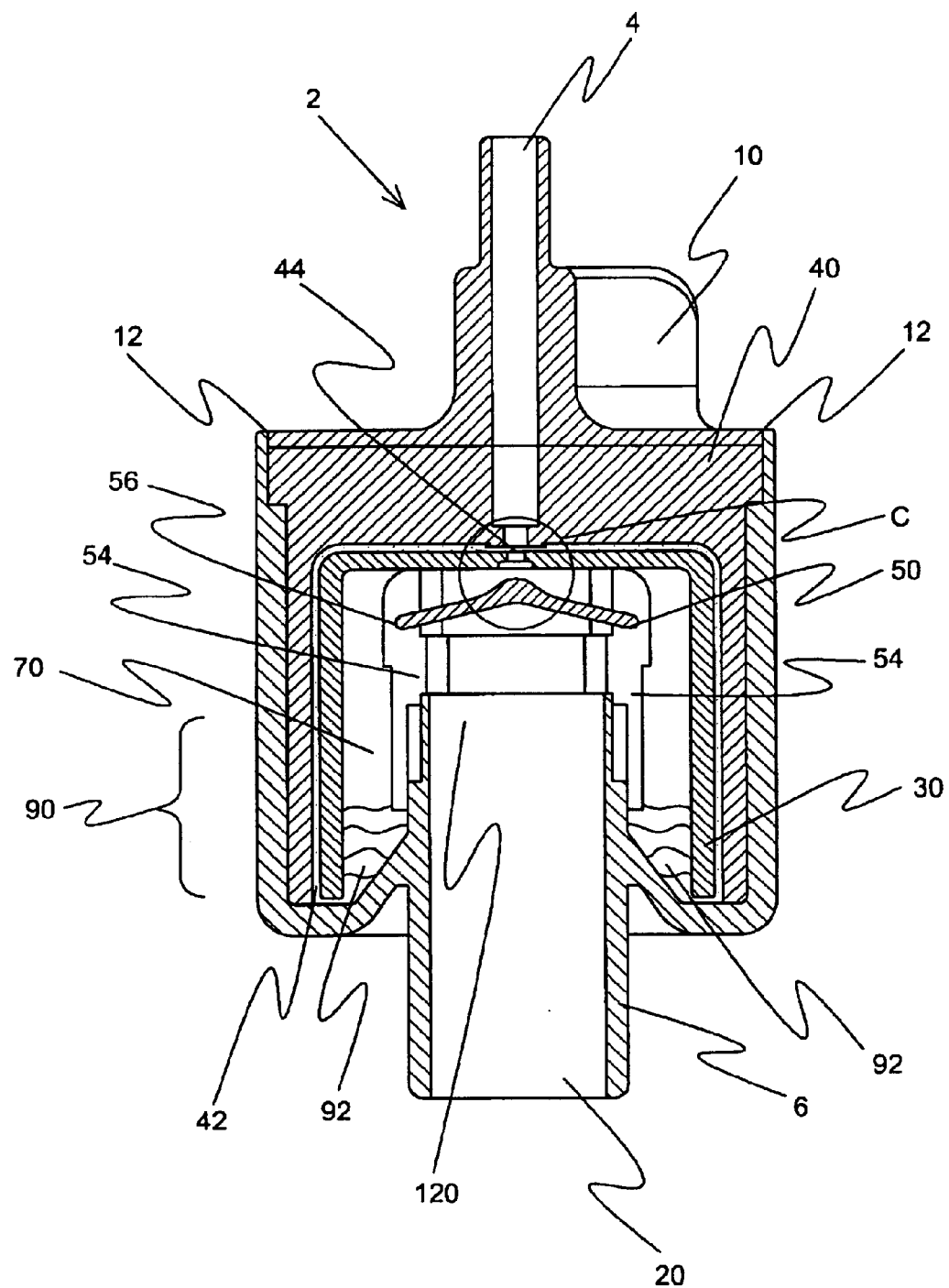
FIG. 3 is a cross-sectional view of the embodiment of FIG. 1, along line A—A.
Figure 4:
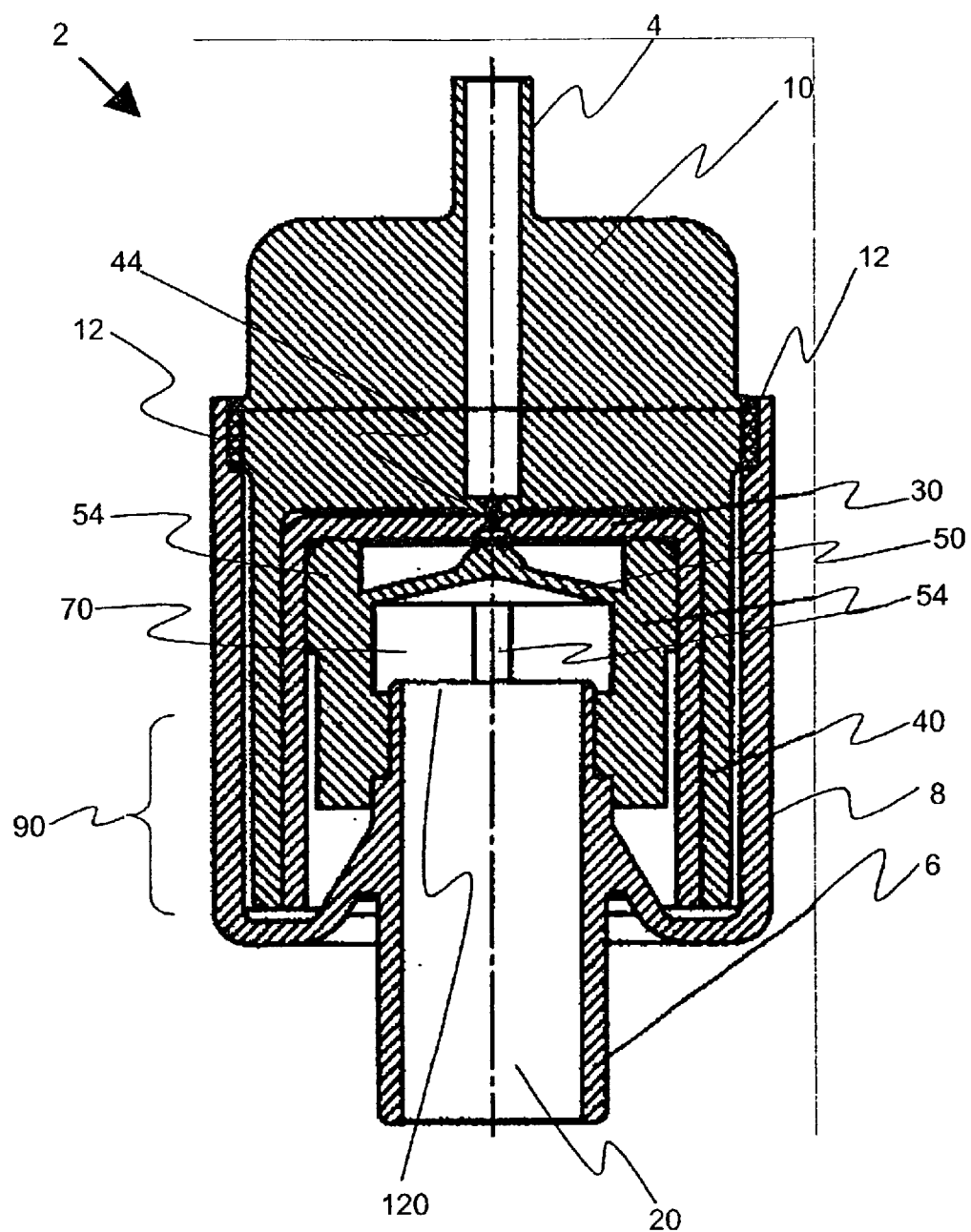
FIG. 4 is a cross-sectional view of the embodiment of FIG. 1, along line B—B.
Figure 5:
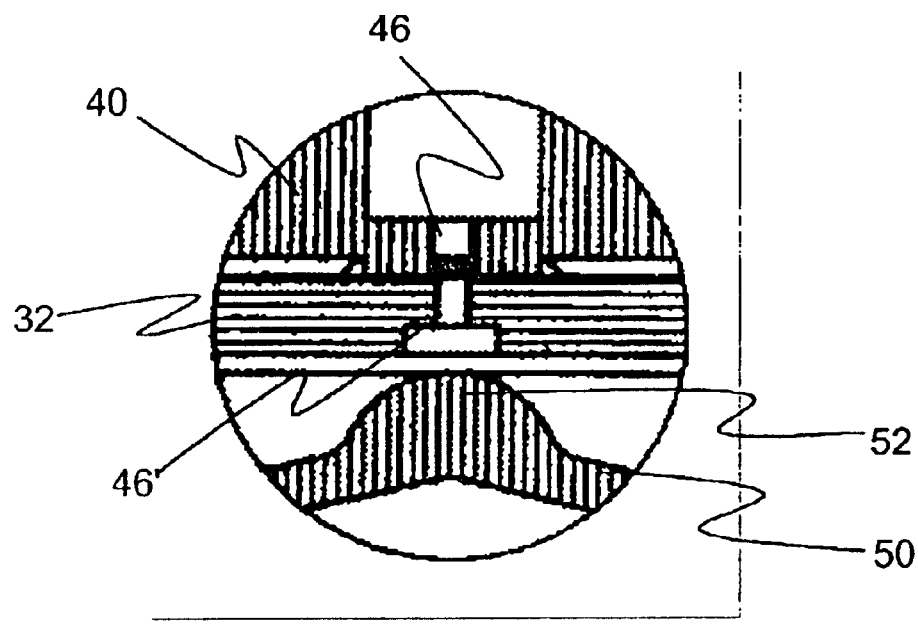
FIG. 5 is a detail of region C of FIG. 3.
Figure 6:
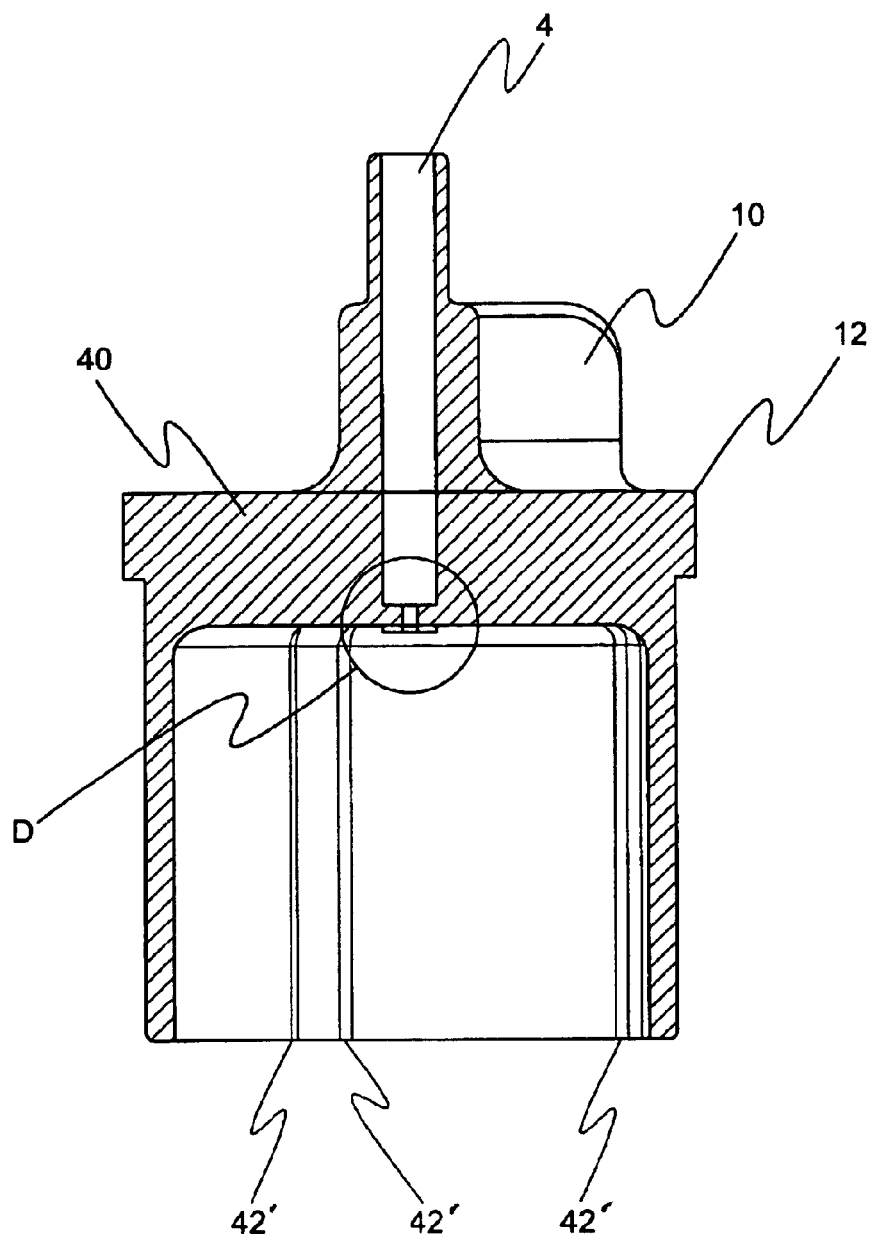
FIG. 6 is a cross-sectional view of an upper housing of the embodiment of FIG. 1 constructed and operative according to the teachings of the present invention, taken along line A—A.
Figure 7:
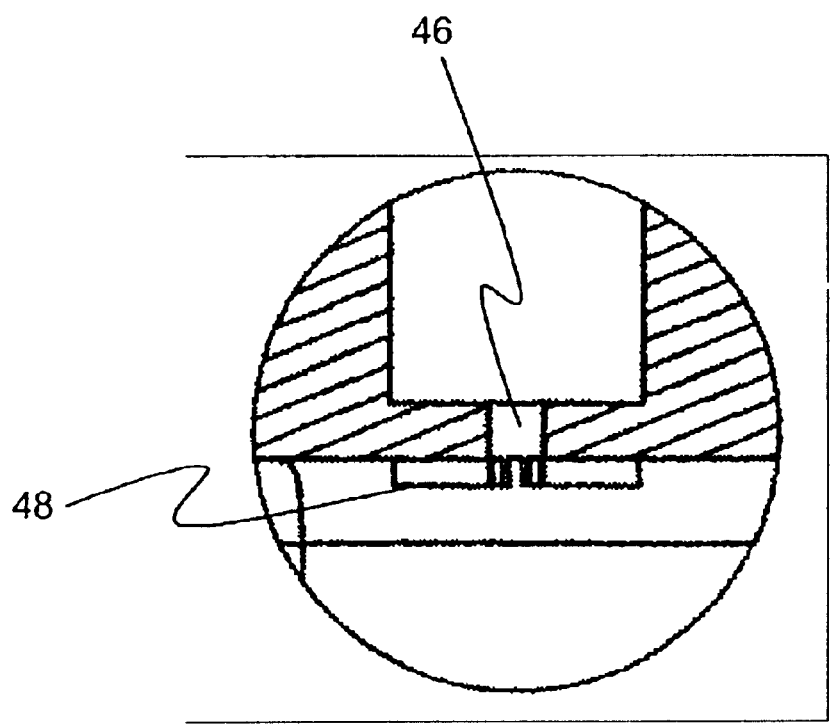
FIG. 7 is a detail of region D of FIG. 6.
Figure 8:
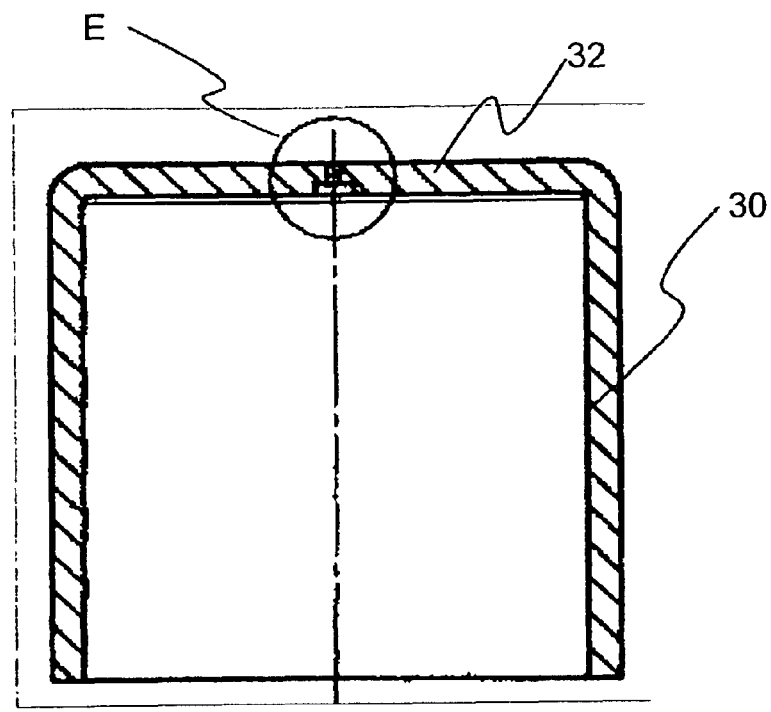
FIG. 8 is a cross-sectional view, taken along line A—A, of a fluid passageway insert constructed and operative according to the teachings of the present invention, for deployment in the upper housing of FIG. 6.
Figure 9:
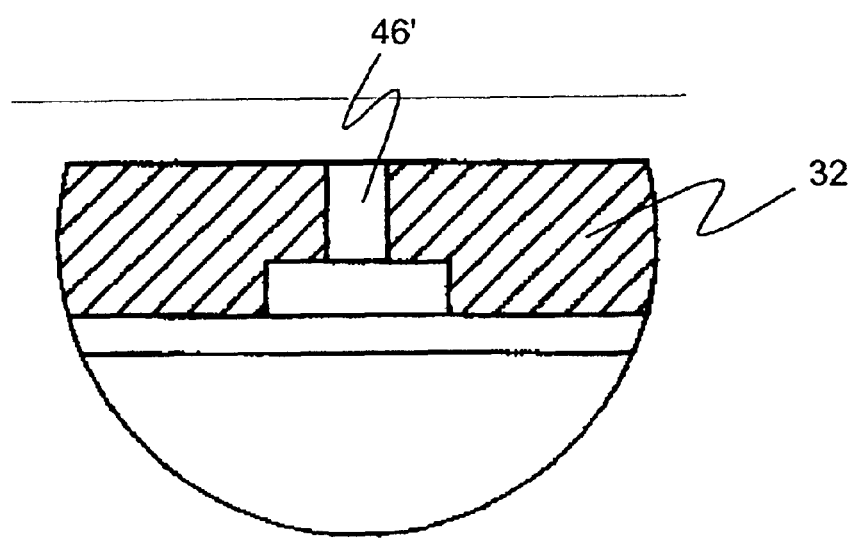
FIG. 9 is a detail of region E of FIG. 8.
Figure 10:
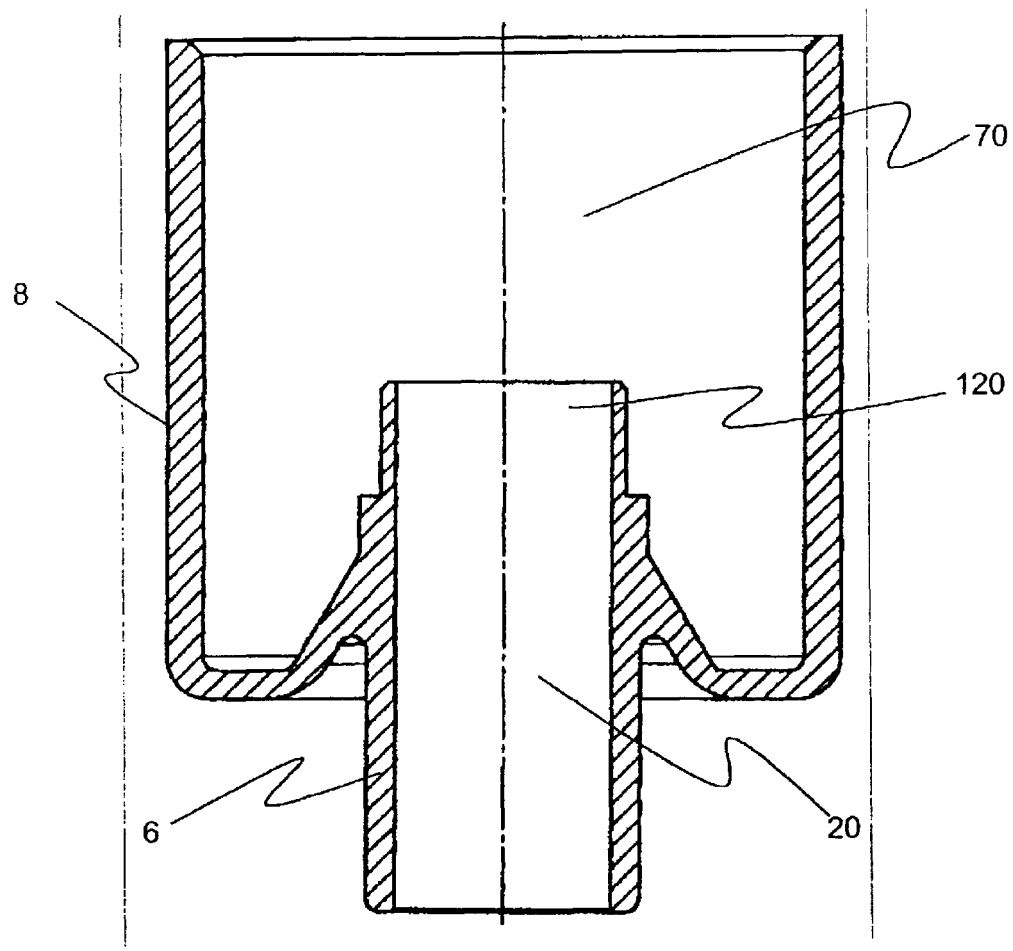
FIG. 10 is a cross-sectional view, taken along line A—A, of a lower housing of the embodiment of FIG. 1 constructed and operative according to the teachings of the present invention.
Figure 11:
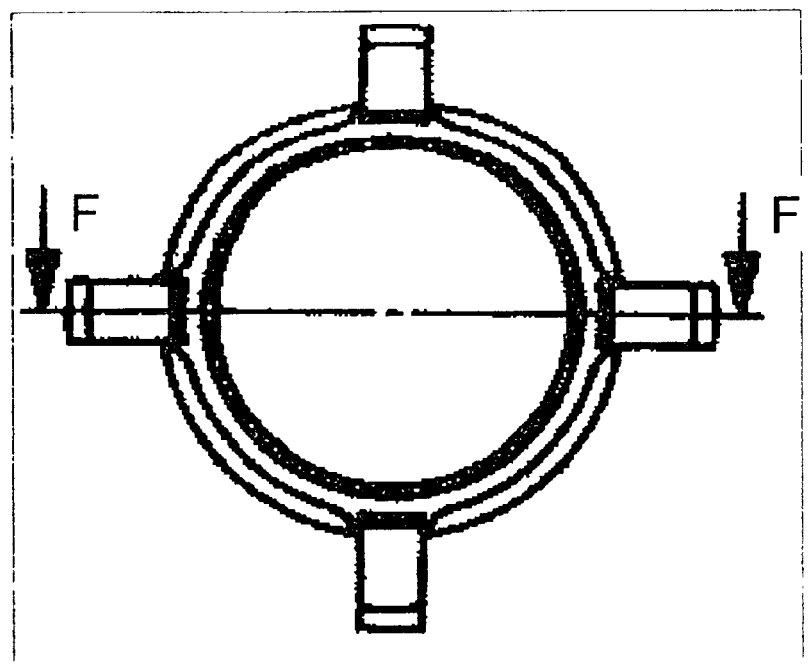
FIG. 11 is a top elevation of an atomization baffle constructed and operative according to the teachings of the present invention, for deployment in the lower housing of FIG. 6, shown to establish cross-sectional line F—F.
Figure 12:
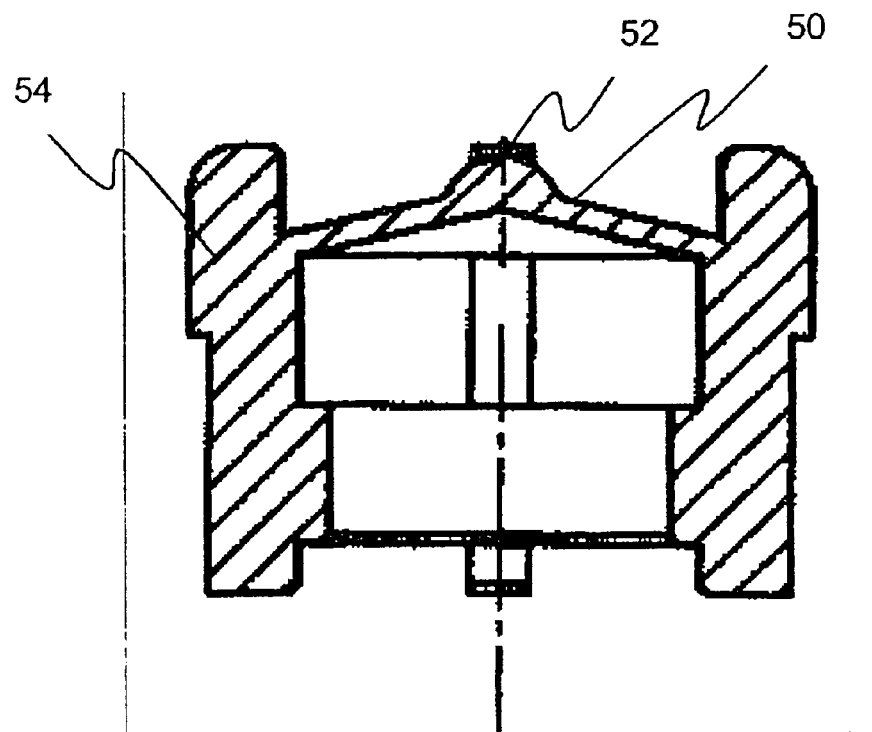
FIG. 12 is a cross-sectional view, taken along line F—F, of the atomization baffle of FIG. 11.
Figure 13:
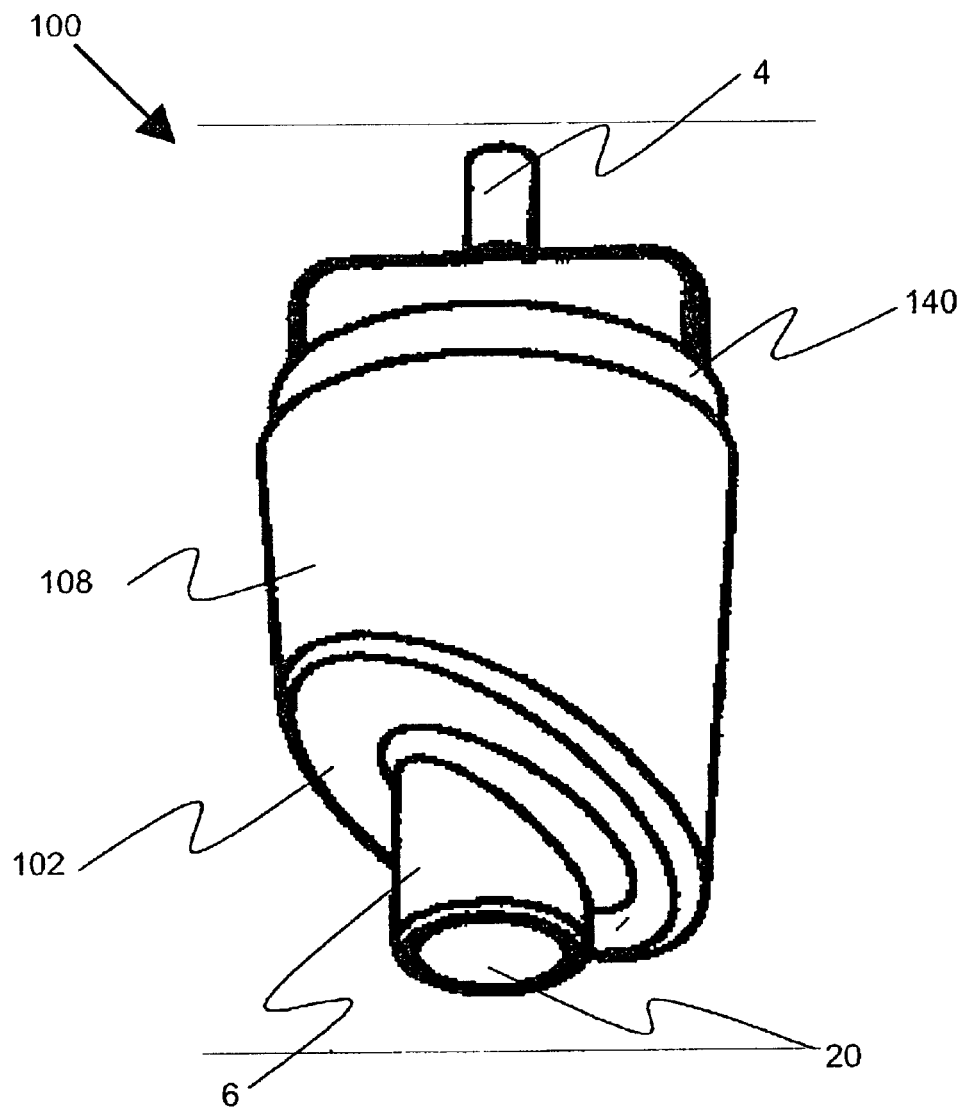
FIG. 13 is a perspective view of a second preferred embodiment of a downdraft nebulizer constructed and operative according to the teachings of the present invention, this embodiment having a reservoir with a sloping bottom.
Figure 14:
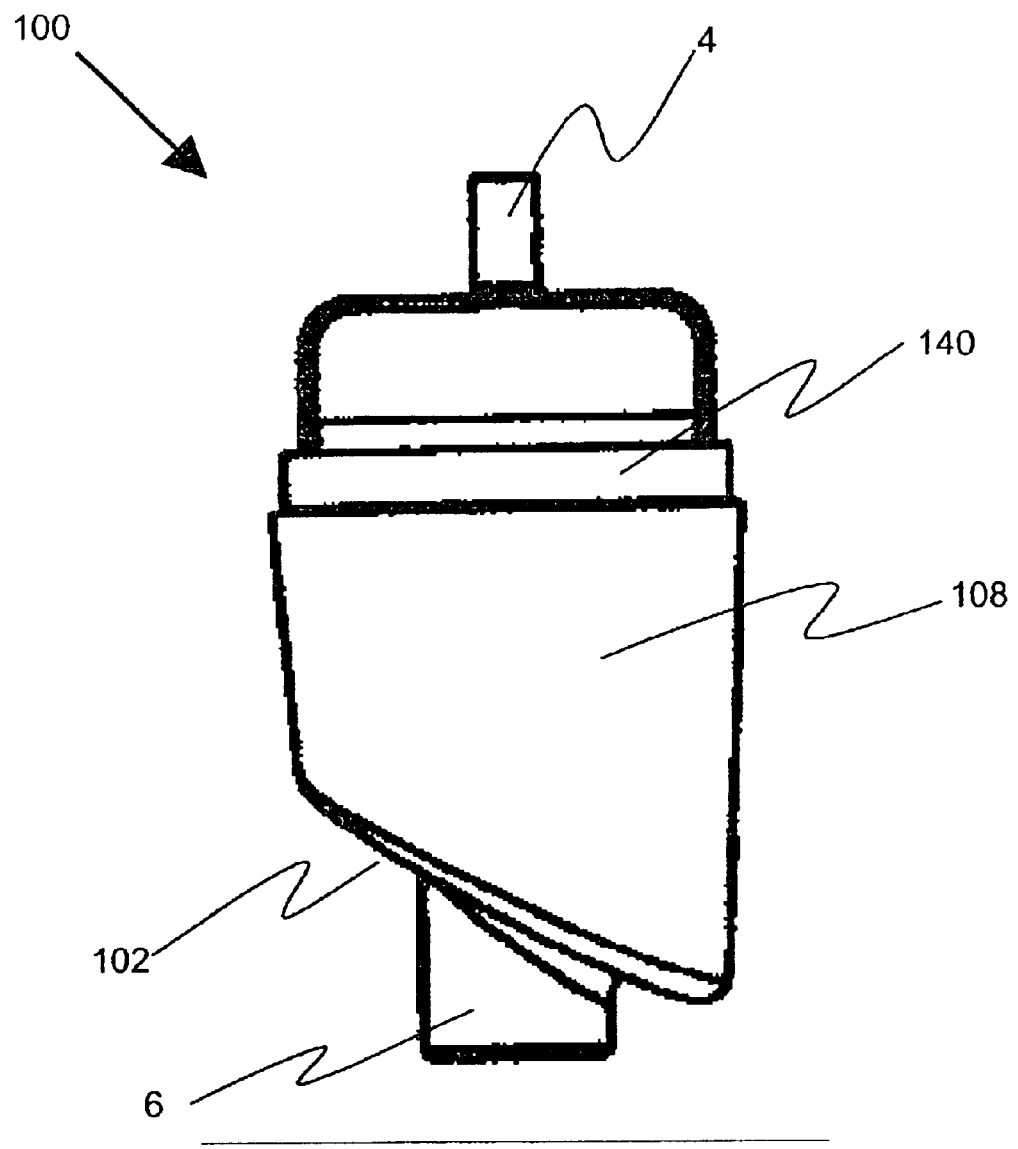
FIG. 14 is a side elevation of the embodiment of FIG. 13.
Figure 15:
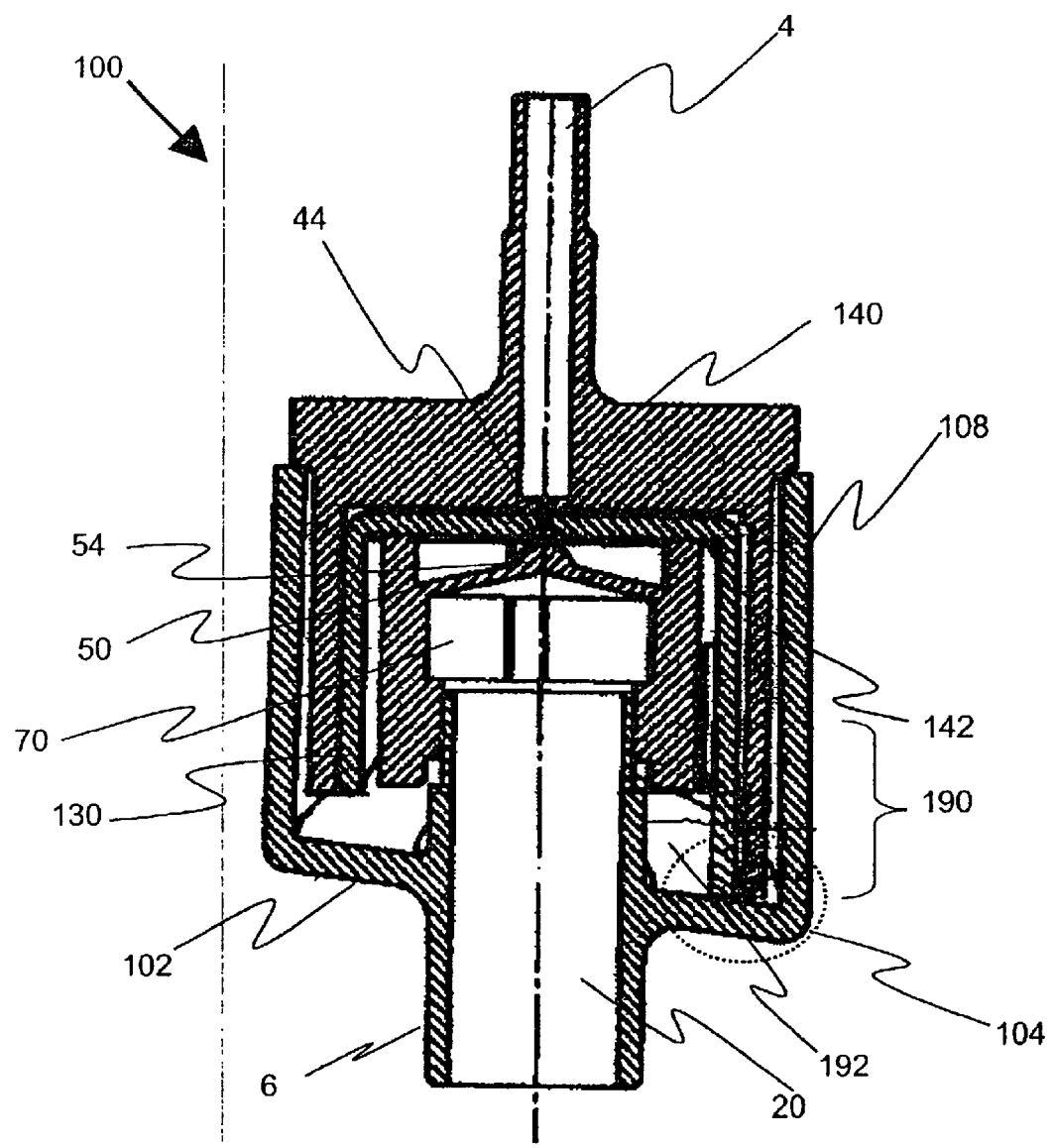
FIG. 15 is a cross-sectional view of the embodiment of FIG. 13.

The present invention a pneumatic nebulizer in which aerosol mist is produced in a downwardly flowing direction, the aerosol mist then leaves the nebulizer through a downwardly projecting aerosol outlet, that is to say, a downdraft nebulizer.

The principles and operation of downdraft nebulizer according to the present invention may be better understood with reference to the drawings and the accompanying description.

By way of introduction, the nebulizers presently in general use are configured for discharge of medication mist either into an inhalation interface or directly into the environment. Typically, the intention of nebulizers used for extended time administration is produce a flow of droplets of medication in atmospheric suspension to an inhalation interface, usually a mouth piece. The medicated mist is generally discharged in an upward or sideward direction since this is the easiest way to deal with the problem of trapping drops that are too large to be aspirated by a patient.

There are, however, applications where a downward flow may be advantageous and even preferred. An application in point is the aerosol inhalation interface that is suspended above the patient, disclosed in WO0202052, to the present inventor. An intention of WO0202052 is to use the force of gravity to draw a medicated mist down to a patient lying beneath a nebulizer within a controlled environment.

Referring now to the drawings, FIG. 1 illustrates the exterior of a first preferred embodiment of a nebulizer, generally referred to herein by 2, constructed and operative according to the teachings of the present invention. High velocity gas, typically compressed air, is introduced into the nebulizer through the air inlet 4 medicated mist is discharged from the nebulizer through the downwardly projecting aerosol outlet passage 20 in the outlet tube 6, which extends downwardly from the lower housing 8. As used herein, the terms "down" and "downward", refer to a direction aligned with the force of gravity.

As mentioned above, FIG. 2 serves to establish cross-sectional lines A—A, along which FIGS. 3, 6, 8, and 10 are taken, and B—B, along which FIG. 4 is taken.

A first preferred embodiment, as discussed herein, includes four structural elements, the deployment of which is illustrated in FIGS. 3 and 4, which are cross-sections across the diameter of a substantially cylindrical housing taken along different lines (see FIG. 2). A substantially cylindrical lower housing 8 includes a downwardly projecting aerosol outlet passageway 20 (for clarity see FIG. 10). Supported above the opening of the aerosol outlet passageway 20 is an atomization baffle 50 (FIGS. 11 and 12). A substantially cylindrical upper housing 40 (FIG. 6) is inserted into the lower housing 8. The inside diameter of the lower housing 8 and the outside diameter of the upper housing 40 as substantially the same so as to create a seal between them. Each of the two housing elements is configured with corresponding threads about their circumferences in region 12 so as to provide for secure interconnection of the two as the upper housing is turned using handle 10. The cylindrical wall of the upper housing extends substantially to the lower interior surface of the lower housing. When thusly interconnected, the two housing elements define within them an interior volume 70, the bottom of which serves as a reservoir 90 for the liquid 92 being, dispensed by the nebulizer. Deployed within the volume 70 is a substantially cylindrical fluid passageway insert 30 (FIG. 8) configured to substantially abut the cylindrical wall of the upper housing 40. The lower edge of the cylindrical wall of the fluid passageway insert 30 is spaced above the lower interior surface of the lower housing 8 enough to allow liquid 92 to flow beneath it.

The upper housing 40 is configured with two structural features. One of these features is a terminal opening 46 (see FIG. 7 for clarity) of the compressed air inlet 4. An outlet of the passageway 46, which is an upper portion of a venturi orifice 44, is circumscribe by a spacer extension 48 that serves to limit the height to which the fluid passageway insert 30 may be inserted into the upper housing 40. The space created between the fluid passageway insert 30 and the upper housing 40 serves as an upper portion of a fluid passageway 42. Another feature is spaced apart grooves 42' (see FIG. 6) in the surface of the cylindrical wall that works in concert with the fluid passageway insert 30 to define vertical portions of fluid passageways 42. Thus, with the fluid passageway insert 30 deployed within the upper housing 40, fluid passages 42, through which fluid communication between the fluid reservoir region 90 of the interior volume 70 of the housing and the venturi orifice 44 may be established, are defined. The lower portion 46' of the venturi orifice 44 is configured in the upper wall 32 of the fluid passageway insert 30. It should be noted that the four grooves 42 that partially define the fluid passageways 42' may be implemented as any number of grooves. Is should be further noted that the grooves 42' described here, and with regard to a second embodiment of the present invention discussed below, may alternately be configured in the fluid passageway insert 30.

Deployed with in the internal volume of the nebulizer, below the opening of the venturi orifice 44 is an atomization baffle 50. The atomization baffle 50 is configured substantially as a disk deployed at an orientation substantially perpendicular to the cylindrical wall defining the side of the internal volume. As illustrated here, and in FIGS. 4, 11 and 12, the atomization baffle 50 is supported by four radially spaced apart legs 54 that rest of the upper end 120 of the aerosol outlet tube 6. It should be noted that the baffle may alternatively be supported by connection to the fluid passageway insert. The upper surface of the atomization baffle 50 is configured with a semispherical protrusion 52 located substantially below and adjacent to the opening of the venturi orifice 44. It should be noted that the protrusion may be of any functionally appropriate shape, such as, but not limited to, conical, geodesic, or flat. The remainder of the upper surface of the atomization baffle 50 is downwardly sloping such that liquid that collects on the surface during the atomization process will flow to the extreme radial edge 56 of the atomization baffle 50 and fall back into the fluid reservoir region 90 of the internal volume 70.

A second embodiment of a nebulizer, generally referred to as 100 constructed and operative according to the teachings of the present invention is illustrated in FIGS. 13–15. The operational principles of this second embodiment are the same as the first embodiment described above, therefore, structural elements effecting the operation are similar to the first embodiment and therefore are numbered accordingly.

The differentiating feature of this second embodiment is the sloping bottom 102 of the lower housing 108. The sloping bottom 102 creates a region of liquid confluence 104 in the liquid reservoir 190. This allows more of the liquid 192 to be aspirated by the fluid passageway 142 which is configured with a bottom opening substantially corresponding to the lowest point in the reservoir. That is, the inside surface of the cylindrical wall of the upper housing has a groove extending upward from an area adjacent to the lowest point to the top of the wall, and the outer surface of the cylindrical wall of the fluid passageway insert abuts substantially the rest of the inside surface of the cylindrical wall of the upper housing.

The sloping bottom also allows for proper operation of the nebulizer at varying orientations other than vertical. In this embodiment the slope of the bottom is preferably 30 degrees from vertical and allows full operation of the nebulizer within a range of orientations between vertical and about 25 degrees from vertical.

In this second embodiment the lower extremities of each of the cylindrical walls of the upper housing 140 and fluid passageway insert 130 lie within planes that are substantially parallel to the plane of the sloping bottom 102 of the lower housing 108. The upper and lower housing elements may be secured by friction or pressure when press together.

The operation of a nebulizer constructed and operative according to the teachings of the present invention, is substantially as follows:

1—Liquid to be atomized in placed in the reservoir region 90 of the lower housing 8, in which the atomization baffle 50 is deployed.

2—The upper housing 40, containing the fluid passageway insert 30, is inserted into the lower housing 8 and secured by turning the upper housing 40 using handle 10.

3—A tube connected to a source of compressed air is connected to inlet 4 and a high velocity flow of air is introduced into the nebulizer.

4—As the high velocity air passes through the venturi orifice 44, liquid from the reservoir 90 is aspirated up through the fluid passageways 42, by a venturi effect, and into the air flow.

5—The introduction of the liquid into the flow of high velocity air causes the liquid to form drops.

6—As the drops flow out of the venturi orifice 44 they are impinged on the surface of the semispherical protrusion 52 of the atomization baffle 50. This causes some of the drops to break up into smaller droplets so as to form a mist.

7—The mist follows a flow path that flows radially outward around the atomization baffle 50.

8—The flow path of the mist turns radially inward toward the top 120 of the downwardly projecting aerosol outlet passageway 20.

9—The mist flows down through the aerosol outlet passageway 20 and out of the nebulizer with a downward flow path.

10—Liquid from drops that where to large to be suspended in the mist fall, by the force of gravity, onto the upper surface of the atomization baffle 50 or directly into the liquid reservoir 90. Any liquid that condenses on the upper surface of the atomization baffle 50 flows to the outer or extreme radial edge 56 of the baffle and fall into the liquid reservoir 90. Liquid that condenses on other surfaces within the interior volume of the nebulizer flows by the force of gravity back into the liquid reservoir 90.

It will be appreciated that the above descriptions are intended only to serve as examples, and that many other embodiments are possible within the spirit and the scope of the present invention.

What is claimed is:

1. A pneumatic nebulizer comprising: (a) at least one downwardly projecting aerosol flow outlet passageway; (b) at least one inlet for introduction of a flow of compressed air; (c) at least one orifice through which said compressed air passes thereby causing a venturi effect; (d) at least one source of liquid in fluid communication with said orifice such that liquid is drawn to said orifice by said venturi effect, said liquid thereby forming into drops and flowing with said compressed air, wherein said source of liquid is a reservoir configured as bottom portion of a volume within a housing of said nebulizer, and (e) at least one baffle upon which said flow of compressed air and drops are impinged so as to atomize said drops into yet smaller droplets thereby forming a mist, said baffle deployed such that a flow path of said mist substantially circumscribes said baffle so as to reach said at least one downwardly projecting aerosol outlet passageway, and (f) wherein at least a top portion of said downwardly projecting aerosol flow outlet passageway extends into said volume.

2. The nebulizer of claim 1, wherein said volume substantially circumscribes at least a portion of said downwardly projecting aerosol outlet passageway.

3. The nebulizer of claim 2, further comprising at least one fluid passageway configured at a radial extremity of said volume through which said fluid communication is established.

4. The nebulizer of claim 3, further including a fluid passageway insert deployed within said volume, said fluid passageway insert configured so as to substantially abut at least one housing surface defining said volume, said at least one fluid passageway configured as at least one surface groove configured in the surface of one of said fluid passageway insert and said housing surface.

5. The nebulizer of claim 4, wherein said volume is configured as a substantially vertical cylindrical volume such that said orifice is configured at a top of said cylindrical volume and said downwardly projecting aerosol outlet passageway is configured at a bottom of said cylindrical volume.

6. The nebulizer of claim 5, wherein said fluid passageway insert is configured substantially as a cylinder having an open end and a closed end such that said closed end is deployed adjacent to said top of said cylindrical volume, and said closed end includes at least a portion of said orifice.

7. The nebulizer of claim 6, wherein said at least one surface groove is implemented as a plurality of circumferentially spaced apart grooves in the surface of one of said fluid passageway insert and said housing surface.

8. The nebulizer of claim 2, wherein said baffle is supported substantially above said downwardly projecting aerosol outlet passageway so as to constitute a flow path obstacle around which said mist flows in order to reach said downwardly projecting aerosol outlet passageway.

9. The nebulizer of claim 8, wherein said baffle is configured substantially as a disk having a diameter larger then a diameter of a top opening of said downwardly projecting aerosol outlet passageway, said baffle being supported above said downwardly projecting aerosol outlet passageway such that an extreme radial edge of said baffle extends beyond said top opening so as to be aligned with a portion of said reservoir.

10. The nebulizer of claim 9, wherein said baffle is supported by a plurality of circumferentially spaced apart support legs.

11. The nebulizer of claim 8, wherein said baffle further includes an upwardly extending protrusion, said baffle being deployed such that said protrusion is deployed substantially under said orifice and in substantially direct alignment with a flow of said high velocity gas and said drops so as to constitute a surface upon which said impingement occurs.

12. The nebulizer of claim 11, wherein a top surface of said baffle is downwardly sloping from said protrusion to said extreme radial edge, such that excess said liquid which accumulates on said baffle flows off said baffle thereby being returned to said reservoir.

13. A method for atomizing a liquid using a pneumatic nebulizer comprising: (a) passing a downward flow of compressed air through at least one orifice thereby causing a venturi effect: (b) providing at least one source of liquid in fluid communication with said at least one orifice such that liquid is drawn to said orifice by said venturi effect, said liquid thereby forming into drops and flowing downwardly with said compressed air, wherein said source of liquid is implemented as a reservoir configured as a bottom portion of a volume within a housing of said nebulizer; (c) providing at least one baffle upon which said downward flow of compressed air and drops are impinged so as to atomize said drops into yet smaller droplets thereby forming a mist, said baffle deployed such that a flow path of said mist substantially circumscribes said baffle so as to reach at least one downwardly projecting aerosol flow outlet passageway, and wherein said volume is implemented so as to substantially circumscribe at least a top portion of said downwardly projecting aerosol outlet passageway.

14. The method of claim 13, further comprising providing at least one fluid passageway configured at a radial extremity of said volume through which said fluid communication is established.

15. The method of claim 14, further comprising providing a fluid passageway insert deployed within said volume, said fluid passageway insert configured so as to substantially abut at least one housing surface defining said volume, said at least one fluid passageway configured as at least one surface groove configured in the surface of one of said fluid passageway insert and said housing surface.

16. The method of claim 15, wherein said volume is implemented as a substantially vertical cylindrical volume such that said orifice is configured at a top of said cylindrical volume and said downwardly projecting aerosol outlet passageway is configured at a bottom of said cylindrical volume.

17. The method of claim 16, wherein said fluid passageway insert is implemented substantially as a cylinder having an open end and a closed end such that said closed end is deployed adjacent to said top of said cylindrical volume, and said closed end includes at least a portion of said orifice.

18. The method of claim 17, wherein said at least one surface groove is implemented as a plurality of circumferentially spaced apart grooves in the surface of one of said fluid passageway insert and said housing surface.

19. The method of claim 13, wherein said baffle is implemented so as to be supported substantially above said downwardly projecting aerosol outlet passageway so as to constitute a flow path obstacle around which said mist flows in order to reach said downwardly projecting aerosol outlet passageway.

20. The method of claim 19, wherein said baffle is implemented substantially as a disk having a diameter larger then a diameter of a top opening of said downwardly projecting aerosol outlet passageway, said baffle being supported above said downwardly projecting aerosol outlet passageway such that a extreme radial edge of said baffle extends beyond said top opening so as to be aligned with a portion of said reservoir.

21. The method of claim 20, wherein said baffle is implemented so as to be supported by a plurality of circumferentially spaced apart support legs.

22. The method of claim 21, further comprising providing an upwardly extending protrusion on a top surface of said baffle, said baffle being deployed such that said protrusion is deployed substantially under said orifice and in substantially direct alignment with a flow of said high velocity gas and said drops so as to constitute a surface upon which said impingement occurs.

23. The method of claim 22, wherein said baffle in implemented having a top surface that is downwardly sloping from said protrusion to said extreme radial edge, such that excess said liquid which accumulates on said baffle flows off said baffle thereby being returned to said reservoir.

* * * * *